(12) United States Patent
Heide

(10) Patent No.: US 10,561,782 B2
(45) Date of Patent: Feb. 18, 2020

(54) MEDICAL DEVICE AND METHOD OF DETECTING THE FILLING LEVEL OF A BUBBLE CHAMBER

(71) Applicant: Fresenius Medical Care Deutschland GmbH, Bad Homburg (DE)

(72) Inventor: Alexander Heide, Eppstein (DE)

(73) Assignee: FRESENIUS MEDICAL CARE DEUTSCLAND GMBH, Bad Homburg (DE)

( * ) Notice: Subject to any disclaimer, the term of this patent is extended or adjusted under 35 U.S.C. 154(b) by 779 days.

(21) Appl. No.: 15/021,377

(22) PCT Filed: Oct. 2, 2014

(86) PCT No.: PCT/EP2014/002687
§ 371 (c)(1),
(2) Date: Mar. 11, 2016

(87) PCT Pub. No.: WO2015/049056
PCT Pub. Date: Apr. 9, 2015

(65) Prior Publication Data
US 2016/0220749 A1    Aug. 4, 2016

(30) Foreign Application Priority Data

Oct. 4, 2013 (DE) .......................... 10 2013 016 469

(51) Int. Cl.
*B01D 46/46*     (2006.01)
*B01D 53/30*     (2006.01)
(Continued)

(52) U.S. Cl.
CPC ........ *A61M 1/3626* (2013.01); *A61M 1/3624* (2013.01); *A61M 1/3638* (2014.02);
(Continued)

(58) Field of Classification Search
None
See application file for complete search history.

(56) References Cited

U.S. PATENT DOCUMENTS 4,170,765 A * 10/1979 Austin .................... G01S 15/14
367/108
5,303,585 A * 4/1994 Lichte ................. G01F 25/0061
367/908

(Continued)

FOREIGN PATENT DOCUMENTS

CN    101784232    7/2010
CN    101842123    9/2010
(Continued)

*Primary Examiner* — Amber R Orlando
*Assistant Examiner* — Phillip Y Shao
(74) *Attorney, Agent, or Firm* — Jacobson Holman, PLLC.

(57) ABSTRACT

The present invention relates to a medical device, in particular to a blood treatment apparatus, having a control and processing unit, having at least one structure-borne sound emitter and having at least one structure-borne sound sensor, each configured for coupling to coupling points of a medical tubing kit which can be coupled to the medical device, wherein the filling level of a bubble chamber arranged in the tubing kit can be determined at the tubing kit via the control and processing unit based on the measurement of the structure-borne sound.

28 Claims, 3 Drawing Sheets

Figure 1:
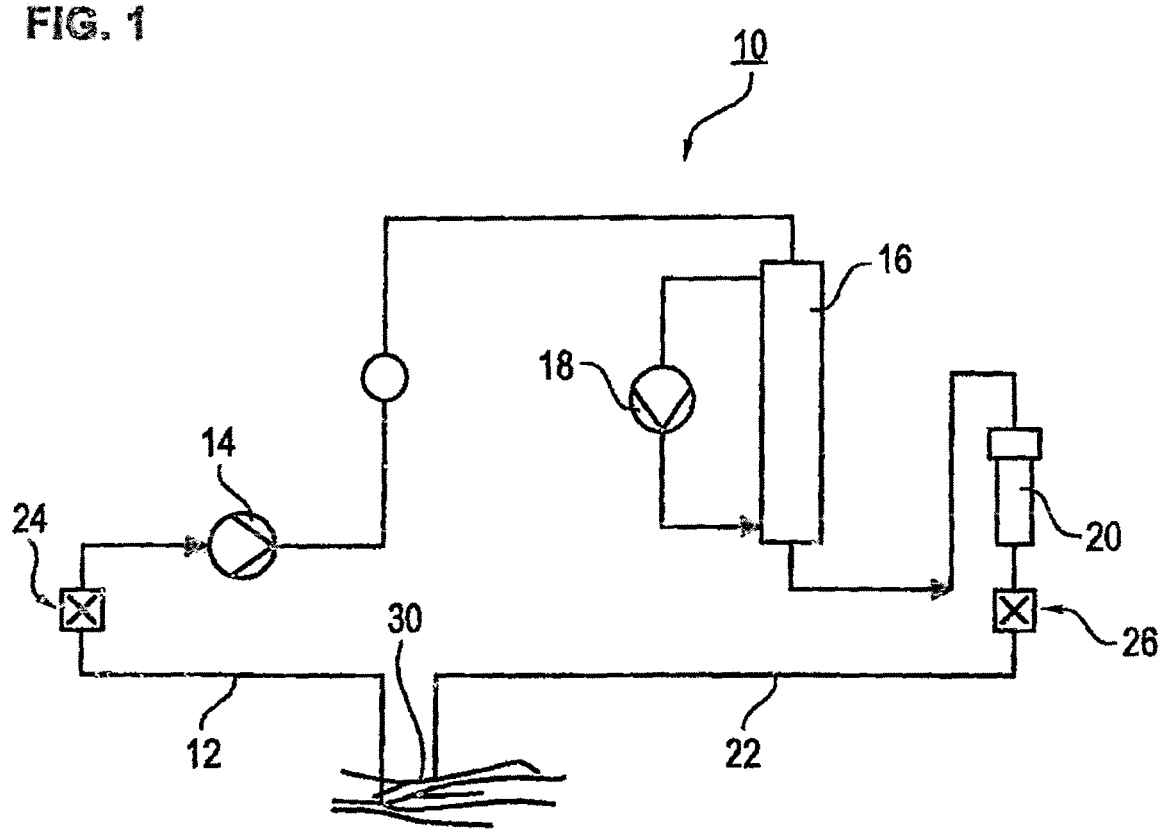

(51) Int. Cl.
*A61M 1/36* (2006.01)
*A61M 1/10* (2006.01)

(52) U.S. Cl.
CPC ... *A61M 1/1039* (2014.02); *A61M 2205/0294* (2013.01); *A61M 2205/14* (2013.01); *A61M 2205/18* (2013.01); *A61M 2205/3375* (2013.01); *A61M 2205/3389* (2013.01); *A61M 2205/50* (2013.01)

(56) References Cited

U.S. PATENT DOCUMENTS

| | | | |
|---|---|---|---|
| 6,090,048 A * | 7/2000 | Hertz | A61M 5/16859 600/485 |
| 6,631,639 B1 * | 10/2003 | Dam | G01F 23/2961 340/621 |
| 2003/0009123 A1 | 1/2003 | Brugger et al. | |
| 2004/0220509 A1 * | 11/2004 | Olsen | A61M 1/32 604/6.14 |
| 2008/0098798 A1 * | 5/2008 | Riley | A61M 5/365 73/19.03 |
| 2011/0112472 A1 * | 5/2011 | Jacobson | A61F 9/00736 604/67 |
| 2011/0257579 A1 | 10/2011 | Rossi et al. | |

FOREIGN PATENT DOCUMENTS

| | | |
|---|---|---|
| CN | 102858388 | 1/2013 |
| DE | 3720667 | 1/1989 |
| DE | 102007039581 | 2/2009 |
| WO | WO 2007/133259 | 11/2007 |
| WO | WO 2009/052496 | 4/2009 |

* cited by examiner

MEDICAL DEVICE AND METHOD OF DETECTING THE FILLING LEVEL OF A BUBBLE CHAMBER

The present invention relates to a medical device, in particular to a blood treatment apparatus, for extracorporeal blood treatment. A medical tubing kit can be coupled to the medical device and at least one medical fluid can be transported through this by the medical device.

Such tubing kits frequently have a bubble chamber which serves to separate any air bubbles which may arise in the fluid circuit formed by the tubing kit from the transported fluid.

Corresponding blood treatment apparatus inter alia have a venous bubble chamber which serves to separate air bubbles which may occur in the extracorporeal blood circuit from the blood and thus to prevent air embolisms on the return of the blood into the patient. The fluid level of the blood in the bubble chamber should, on the one hand, not fall below a specific minimal value so that the bubble chamber does not run empty and should, on the other hand, not exceed a specific maximum value so that the bubble chamber is not completely filled with fluid, but rather that a fluid level is always present. The filling level must therefore be constantly monitored. The level in a bubble chamber is as a rule adjusted as required by adding or removing air in the region above the solubility level. For example, ultrasound sensors are located at the receiver of the venous blood chamber at the machine side for monitoring the filling level of the venous bubble chamber. A conclusion on the filling level of the venous chamber can be drawn from the change of the ultrasonic signal. This ultrasound technique at the machine side is, however, complex and/or expensive and has to be reliably coupled to the venous blood chamber. The ultrasound measurement in particular requires a correct insertion of the bubble chamber into the receiver on the machine side so that the bubble chamber adopts a defined position with respect to the ultrasound sensors. This, on the one hand, requires corresponding construction measures for the spatial fixing of the bubble chamber to the blood treatment apparatus and, on the other hand, an attentive setting up of the blood tubing kit at the blood treatment apparatus. This workstep nevertheless remains prone to error so that incorrect measurements of the filling level can occur.

Instead of a detection of the level in a bubble chamber, it is known from DE 37 20 667 A1 to detect the presence of air bubbles in the blood stream which flows through the blood tubing kit by an ultrasound measuring section arranged before the bubble chamber and coupled to the blood tubing kit. The signals of the ultrasound measuring section are then totaled and compared with limit values in order to trigger an alarm as necessary.

The use of an ultrasound measuring section for the detection of air bubbles in the blood stream is known from US 2003/0009123 A1. Ultrasound emitters and transmitters are used in US 2008/0195021 A1 to detect a needle disconnection.

It is now the object of the present invention to further develop the detection of the level in a bubble chamber, for example in a venous bubble chamber of an extracorporeal blood circuit, which is part of the disposable blood tubing kit for the carrying out of an extracorporeal blood treatment, such that it can be carried out simply and with a reliable operation.

This object is achieved in accordance with the invention by a medical device having the features of in accordance with the following description. A medical device is accordingly provided having a control and processing unit which has at least one structure-borne sound emitter and at least one structure-borne sound sensor, wherein they are respectively configured such that they can be coupled to coupling points of a medical tubing kit which can be coupled to the medical device, wherein the status of a section of the tubing kit can be determined via the control and processing unit on the basis of the measurement of the structure-borne sound at the tubing kit.

This solution in accordance with the invention is based on the evaluation of structure-borne sound which propagates in the tubing kit. Such evaluations of the propagation of structure-borne sound in the tubing kit can be used, for example, for monitoring the integrity of the tubing kit. The structure-borne sound can be coupled into the blood tubing kit at the medical device, for example, by means of a sound wave.

Experiments have surprisingly shown that the structure-borne sound not only propagates via the fluid in the blood tubing kit, but is also largely forwarded over long paths in the walls of the tube and in the walls of the components of the tubing kit such as in the walls of the bubble chamber and in the walls of the dialyzer. In this respect, the walls of the components, however, have more of a damping effect on the sound propagation in comparison with the sound conduction of the fluid in the tubing kit. The invention utilizes these properties.

The filling level of a bubble chamber arranged in the tubing kit can be determined as the status of the section of the extracorporeal blood circuit. This aspect of the invention takes account of the fact that the damping behavior of the bubble chamber is amplified significantly and reproducibly as the filling level falls. The higher the filling level is, the lower the damping. The present invention is therefore based on the fact that a conclusion is drawn from the measured damping behavior of the bubble chamber on its filling level. The damping behavior is determined in that the amplitude of the structure-borne sound is measured downstream of the bubble chamber to be measured in a sound propagation direction, with the measured structure-borne sound being damped at different levels in dependence on the filling level on passing through the bubble chamber.

In accordance with the invention, in this respect, the structure-borne sound coupled into the tubing kit via the structure-borne sound emitter and propagating in the fluid circuit can be taken up via the structure-borne sound sensor and can be conducted to the control and processing unit for determining the filling level. The filling level of the bubble chamber is therefore in particular determined by evaluating a signal of the structure-borne sound sensor.

In accordance with a possible embodiment of the present invention, the control and processing unit determines the filling level of the bubble chamber by a comparison with at least one stored characteristic. Such a characteristic, which can reproduce the filling level in dependence on the measured amplitude of the signal of the structure-borne sound sensor can be stored in a memory of the medical device. In this respect, a plurality of characteristics can be implemented in the medical device which are used for different tubing kits usable with the medical device. The medical device in this respect preferably comprises a detection device for detecting the coupled tubing kit, in particular an input unit or a sensor, with the characteristic being selected in dependence on the detected tubing kit.

In accordance with a first embodiment of the present invention, the structure-borne sound emitter is an occluding pump, in particular a roller pump, which can be coupled to a pump section of the tubing kit. Such occluding pumps generate pressure signals which propagate as structure-borne sound in the tubing kit.

In accordance with a second embodiment of the present invention, the structure-borne sound emitter is an electronically controlled sound generator. In this respect, a control signal which the sound generator converts into structure-borne sound is in particular generated by the control and processing unit. The sound generator preferably comprises a piezo-element. The sound generator can in this respect be couplable to the tubing kit upstream or downstream of a pump. The pump can in this case also be a non-occluding pump, in particular an impeller pump.

In this respect, in particular a separate structure-borne sound signal having a defined frequency can be fed in. A sinusoidal frequency in the frequency range of at least 80 Hz, in particular 160 Hz, has proved particularly suitable for the feed into the tubing kit. A rectangular pulse signal is also suitable.

A piezo film sensor is, for example, suitable as a structure-borne sound sensor which can be coupled to the tubing kit.

In a further embodiment of the present invention, two structure-borne sound emitters can also be provided. They preferably generate different signals so that the signals transmitted by the two structure-borne sound emitters remain distinguishable in the measured signal. For example, in this respect, an occluding pump can be used as a first structure-bound sound emitter and an electronically controlled sound generator can be used as a second structure-borne sound emitter.

In accordance with a further aspect of the invention, the integrity of the tubing kit and/or of the fluid circuit formed by means of the tubing kit can be used as the status of the section of the tubing kit overall.

The at least one emitter and the at least one sensor can advantageously be integrated in the medical device such that they can respectively be coupled to provided coupling points at the tubing kit on insertion of a tubing kit.

The filling level of any fluid, in particular of blood, physiological saline, priming fluid, substitution fluid or medication solution, can in particular be able to be determined in the bubble chamber. The present invention can therefore be used in any desired medical devices in which a tubing kit having a bubble chamber is used.

In a preferred embodiment, the medical device is a blood treatment apparatus. It can in this respect in particular be a dialyzer. The tubing kit can in this respect for example, be a blood tubing kit, a dialyzate tubing kit, a substituate tubing kit and/or a filtrate tubing kit.

The medical device is particularly preferably a blood treatment apparatus for the extracorporeal blood treatment and the tubing kit an extracorporeal blood tubing kit.

In accordance with an aspect of the present invention, the control and processing unit can in this respect monitor the status of a patient port in addition to the filling level determination. The monitoring of the patient port in particular also takes place on the basis of the measurement of the structure-borne sound at the tubing kit and in particular by an evaluation of the signal of the structure-borne sound sensor.

The control and processing unit in this respect in particular detects a needle disconnection when the sound propagation in the extracorporeal blood circuit changes due to the defective patient port and/or when the measured amplitude of the structure-borne sound reduces or is missing. A venous needle disconnection can in particular be detected in this respect.

In the case of a venous needle disconnection, a reduction in the measured amplitude of the structure-borne sound by around 30% can be expected at an extracorporeal blood circuit so that in this error case a significant indication of a venous needle disconnection is present. The control and processing unit in particular therefore concludes a needle disconnection when a reduction is recognized in the measured amplitude of the structural-borne sound by a threshold value which lies between 20% and 60% of the measured amplitude and/or of a base signal.

Provision is made in a preferred embodiment that the control and processing unit stops the blood pump and/or triggers an alarm on detection of a needle disconnection.

In accordance with the invention, the signal of the structure-borne sound sensor can be evaluated in different manners for monitoring the patient port and for the simultaneous determination of the filling level of the bubble chamber. In this respect, different signal portions and/or changes in the signal differing in their time development are preferably associated with the two different aspects.

In this respect, the signal for detecting a needle disconnection can be monitored for faster amplitude changes, while changes of the filling level of the bubble chamber can be detected with reference to slower amplitude changes.

The present invention here makes use of the fact that the measured amplitude admittedly falls or rises in dependence on the level status in the bubble chamber, which, however, occurs continuously and at a much lower frequency and level than the amplitude leap which occurs on a needle disconnection. The two processes can therefore be easily distinguished from one another by a corresponding evaluation of the signal of the structure-borne sound sensor.

The currently measured signal can in this respect be compared with a base signal for detecting a needle disconnection. This is preferably updated during the course of the treatment and/or is formed on the basis of an average time value. The base signal thus reproduces the change of the measured signal on the basis of changes of the level status in the bubble chamber.

In this respect, the base signal can be updatable after a controlled change of the level in a bubble chamber of the extracorporeal blood circuit and in particular after a venting of the bubble chamber. The updating is preferably carried out in an automated process by the control and processing unit.

The base signal which is used for determining the level status and/or for comparison with the currently measured signal is in this respect preferably formed on the basis of an average time value of the measured signal.

In accordance with the present invention, a single structure-borne sound emitter can be used in this respect whose signal propagates over the extracorporeal blood tubing kit and the patient port up to the structure-borne sound sensor.

The signal can propagate in two paths; on the one hand, via the extracorporeal blood tubing kit and, on the other hand, via the patient port to the structure-borne sound sensor. In this respect, the structure-borne sound can in particular propagate on a first path via the extracorporeal blood tubing kit through the bubble chamber to the structure-borne sound sensor and, on the other hand, via a second path via the patient port to the structure-borne sound sensor, without passing through the bubble chamber.

The signal can in this respect, however, also propagate over only one path via the extracorporeal blood tubing kit and via the patient port to the structure-borne sound sensor.

In this respect, the structure-borne sound can in particular pass through the bubble chamber before or after passing the patient port.

In accordance with the invention, however, two structure-borne sound emitters having different signal developments can also be used, in particular an occluding blood pump and a further structure-borne sound emitter arranged upstream or downstream of the blood pump.

The signal portions respectively attributable to the structure-borne sound emitters and for monitoring the patient port as well as for the simultaneous determination of the filling level of the bubble chamber are preferably evaluated separately. The signal of the one structure-borne sound emitter can in particular propagate more on a first path via the extracorporeal blood tubing kit through the bubble chamber to the structure-borne sound sensor and the signal of the other structure-borne sound emitter on a second path via the patient port to the structure-borne sound sensor without passing through the bubble chamber. The signal which passes through the patient port is therefore not influenced by the filling level of the bubble chamber.

In accordance with another aspect of the invention, protection is claimed for a medical device having a tubing kit, in particular a blood treatment machine having a blood tubing kit, as was described above, wherein the tubing kit has at least one coupling point for a structure-borne sound emitter and at least one coupling point for a structure-borne sound sensor. The coupling point for the structure-borne sound emitter is advantageously arranged upstream of the blood pump at the arterial branch of the blood tubing kit or the blood pump serves as the structure-borne sound emitter.

In accordance with a further aspect of the invention, the coupling point for the structure-borne sound sensor is arranged downstream of the venous bubble chamber. As a rule, the structure-borne sound will propagate simultaneously, starting from the machine-side structure-borne sound emitter, both in the arterial branch and in the venous branch of the extracorporeal blood tubing kit, so that sound waves are also incident on the structure-borne sound sensor which have not passed through the bubble chamber. It is decisive for the operation of the invention that at least some of the structure-borne sound waves pass through the bubble chamber and are damped before they are incident on the structure-borne sound sensor.

In accordance with a further aspect of the invention, the coupling point for the structure-borne sound sensor is arranged upstream of the venous bubble chamber. In this case, the sound waves which propagate from the structure-borne sound emitter via the patient port into the venous line pass through the bubble chamber before arriving at the structure-borne sound emitter. The measured signal thus comprises signal portions which are based on passing through the bubble chamber and signal portions which are based on passing through the patient port. As described above, the changes due to a level change in the bubble chamber and the changes due to a needle disconnection can, however, be distinguished from one another.

The use of the invention is naturally not restricted to venous bubble chambers, but can rather also take place at different points of the extracorporeal blood circuit, for example also in the arterial branch of the extracorporeal blood circuit. A structure-borne sound sensor then has to be arranged in the arterial bubble chamber such that at least some of the structure-borne sound waves pass through the arterial bubble chamber before they are incident on the structure-borne sound sensor.

In accordance with the invention, the use of ultrasound sensors at the bubble chamber for determining the fluid filling level can therefore be dispensed with.

The control and processing unit of the blood treatment apparatus advantageously has a data memory in which a computer program is stored. The program code of the computer program is programmed to control the structure-borne sound emitter and to evaluate the signals of the at least one structure-borne sound sensor. The transmission behavior in an error-free state of the section of the extracorporeal blood circuit can be stored as a reference in the data memory so that a conclusion can be drawn on an error-free state of the section on a deviation of the current measured values from the reference.

A further aspect of the invention relates to a method of detecting the filling level of a bubble chamber in a fluid circuit of a medical device, in particular in an extracorporeal blood circuit in a blood treatment apparatus. In this method, a structure-borne sound is coupled via a structure-borne sound emitter into a tubing kit via a coupling point before the bubble chamber. The structure-borne sound propagating in the fluid circuit is taken up via a structure-borne sound sensor coupled to a coupling point arranged after the bubble chamber in the propagation direction of the structure-borne sound and is forwarded to a control and processing unit for determining the filling level.

The filling level of the fluid in the bubble chamber is advantageously determined in the control and processing unit by a comparison with stored characteristics.

Finally, the invention relates to a computer program product having a source code for carrying out the aforesaid method when the computer program is running in the control and processing unit.

As already previously stated, the present invention is suitable for achieving the initially stated object. It is, however, not restricted to the determination of the filling level in bubble chambers. Very generally, the invention namely allows the determination of the status of a section of the extracorporeal blood circuit on the basis of the measurement of structure-borne sound at the extracorporeal blood circuit.

In addition to a bubble chamber, the patient port can also be monitored as the section of the extracorporeal blood circuit in accordance with the invention which can be applied to the patient as a fistula or as a shunt.

The present invention in this respect relates to a blood treatment apparatus for extracorporeal blood treatment having a control and processing unit, having at least one structure-borne sound emitter and having at least one structure-borne sound sensor, each configured for coupling to coupling points of an extracorporeal blood tubing kit coupled to the blood treatment apparatus, wherein the status of a patient port can be determined via the control and processing unit on the basis of the measurement of the structure-borne sound at the extracorporeal blood circuit.

An unknown venous needle disconnection from the patient port can result in a feared free-flow of the blood from the venous needle into the environment if the blood pump is still pumping. If such a serious fault is not recognized immediately, the patient can bleed to death in a few minutes at typical blood flows of 200 ml/min to 300 ml/mm. While a disconnection of the arterial needle is recognized immediately and reliably by the air bubble detectors always present for the prevention of air embolisms due to the environmental air necessarily sucked into the extracorporeal blood circuit from the environment, the reliable recognition of a venous needle disconnection still represents a technical challenge despite many known solution approaches because the frequency of false positive alarms (i.e. corresponding false alarms) simultaneously has to be minimized.

It is possible in this respect in accordance with a further aspect of the invention to detect a needle disconnection, in particular an arterial and/or venous needle disconnection, when the sound transmission in the extracorporeal blood circuit varies due to the defective patient port and when the measured amplitude of the structure-borne sound reduces or is even lost. Such a method is known from WO 97/10013 A1 in which the transfer of the pressure pulses generated by an occluding blood pump is monitored via the patient port.

It is the object of the present invention with respect to this document to reduce the risk of a false alarm and nevertheless to ensure a reliable detection of a needle disconnection.

This object is achieved by a blood treatment apparatus and by a method in accordance with the following aspects. Protection is also claimed for these aspects independently of the above-shown aspects of the present invention.

1. A blood treatment apparatus for the extracorporeal blood treatment having a control and processing unit, having at least one structure-borne sound emitter and having at least one structure-borne sound sensor, each configured for coupling to coupling points of an extracorporeal blood tubing kit coupled to the blood treatment apparatus, wherein the status of a patient port can be monitored via the control and processing unit on the basis of the measurement of the structure-borne sound at the extracorporeal blood circuit, characterized in that
    the currently measured signal is compared with a base signal, which is updated during the course of the treatment, in the control and processing unit for detecting a needle disconnection.
2. A blood treatment apparatus in accordance with aspect 1, wherein the base signal is updated at regular intervals and/or continuously by the control and processing unit.
3. A blood treatment apparatus in accordance with aspect 1 or aspect 2, wherein the base signal can be updated after a controlled change of the level in a bubble chamber of the extracorporeal blood circuit and in particular after a venting of the bubble chamber, wherein the updating is preferably carried out in an automated manner by the control and processing unit.
4. A blood treatment apparatus in accordance with one of the preceding aspects, wherein the control and processing unit forms an average time value of the measured signal for updating the base signal.
5. A blood treatment apparatus in accordance with one of the preceding aspects, wherein the comparison of the currently measured signal with a base signal comprises an amplitude comparison, wherein the amplitude of the currently measured signal is preferably compared with a base amplitude value.
6. A blood treatment apparatus in accordance with one of the preceding aspects, wherein the control and processing unit extracts a signal portion of the measured signal for the comparison of the currently measured signal with a base signal.
7. A blood treatment apparatus in accordance with one of the preceding aspects, wherein the control and processing unit detects a needle disconnection when the sound propagation in the extracorporeal blood circuit changes due to the defective patient port and/or the measured amplitude of the structure-borne sound reduces or is missing, wherein it preferably stops the blood pump and/or triggers an alarm on detection of a needle disconnection.
8. A blood treatment apparatus in accordance with one of the preceding aspects, wherein the structure-borne sound emitter is an occluding pump, in particular a roller pump, which can be coupled to a pump section of the tubing kit, and/or wherein the structure-borne sound emitter is an electronically controlled sound generator which preferably comprises a piezo-element and/or which can preferably be coupled upstream or downstream of a pump at the tubing kit.
9. A blood treatment apparatus in accordance with one of the preceding aspects having a blood tubing kit which has at least one coupling point for a structure-borne sound emitter and has at least one coupling point for a structure-borne sound sensor, wherein the coupling point for the structure-borne sound emitter is arranged at the arterial branch of the blood tubing kit upstream of the blood pump and/or the blood pump serves as a structure-borne sound emitter and/or wherein the coupling point for the structure-borne sound sensor is arranged downstream or upstream of the venous bubble chamber.
10. A method of monitoring the status of a patient port of an extracorporeal blood circuit of a blood treatment apparatus for the extracorporeal blood treatment, wherein the status of the patient port is monitored on the basis of the measurement of structure-borne sound at the extracorporeal blood circuit, characterized in that
    the currently measured signal is compared with a base signal, which is updated during the course of the treatment, for detecting a needle disconnection.
11. A method in accordance with aspect 10, wherein the base signal is updated at regular intervals and/or continuously and/or wherein the base signal is updated after a controlled change of the level in a bubble chamber of the extracorporeal blood circuit and in particular after a venting of the bubble chamber and/or wherein an average time value is used for updating the base signal.
12. A method in accordance with one of the preceding aspects, wherein the comparison of the currently measured signal with a base signal comprises an amplitude comparison, wherein the amplitude of the currently measured signal is preferably compared with a base amplitude value.
13. A method in accordance with one of the preceding aspects, wherein a signal portion of the measured signal is extracted and is compared with the base signal for the comparison of the currently measured signal with a base signal.
14. A method in accordance with one of the preceding aspects, wherein a needle disconnection is detected when the sound propagation in the extracorporeal blood circuit changes due to the defective patient port and/or the measured amplitude of the structure-bound sound decreases or is missing, wherein the blood pump is preferably stopped and/or an alarm is triggered on detection of a needle disconnection, and/or wherein the signal of an occluding pump, in particular of a roller pump, which is coupled to a pump section of the tubing kit, propagating through the extracorporeal blood circuit and the patient port is measured, and/or wherein the signal of an electronically controlled sound generator which preferably comprises a piezo-element and/or which is preferably coupled upstream or downstream of a pump at the tubing kit, propagating through the extracorporeal blood circuit and the patient port is measured, and/or wherein the structure-borne sound emitter is coupled to the arterial branch of the blood tubing kit upstream of the blood pump and/or the blood pump serves as a structure-borne sound emitter, and/or wherein the structure-borne sound sensor is coupled downstream or upstream of the venous bubble chamber.

15. A method in accordance with one of the preceding aspects for monitoring the status of a patient port of an extracorporeal blood circuit of a blood treatment apparatus in accordance with one of the aspects 1 to 9.

In this respect, the present invention comprises a blood treatment apparatus for the extracorporeal blood treatment having a control and processing unit, having at least one structure-borne sound emitter and having at least on structure-borne sound sensor, each configured for coupling to coupling points of an extracorporeal blood tubing kit which can be coupled to the blood treatment apparatus. In this respect, the status of a patient port can be monitored via the control and processing unit on the basis of the measurement of the structure-borne sound at the extracorporeal blood circuit. The patient port can be a fistula or a shunt via which the extracorporeal blood tubing kit is connected to the patient. In accordance with the invention, the control and processing unit in this respect compares the currently measured signal with a base signal, which is updated during the course of the treatment, for the detection of a needle disconnection.

The present invention is in this respect based on the recognition that the structure-borne sound signal measured at the structure-borne sound sensor is not only influenced by the status of the patient port, but also by processes in the blood tubing kit itself. Experiments have surprisingly shown in this respect that the structure-borne sound not only propagates via the fluid in the blood tubing kit, but is also largely forwarded over longer paths in the walls of the tube and in the walls of the components of the blood tubing kit and in particular also in the walls of a bubble chamber. In this respect, the walls of the components, however, have more of a damping effect on the sound propagation in comparison with the sound conduction of the fluid in the blood tubing kit. The present invention therefore takes into account that the sound propagation in the extracorporeal blood tubing kit can change during the duration of the treatment in dependence on the filling level of the components used there and in particular in dependence on the filling level of a bubble chamber arranged in the extracorporeal blood tubing kit.

The updating of the base signal in accordance with the invention with which the currently measured signal is compared for detecting a needle disconnection now provides that such changes resulting during the course of the treatment are taken into account in the transfer behavior of the blood tubing kit and thus neither trigger a false alarm nor negatively influence the security of a detection of a needle disconnection.

In accordance with a possible embodiment of the present invention, the base signal is in this respect updated at regular intervals and/or continuously by the control and processing unit. Since the above-described changes in the blood tubing kit such as the filling level of a bubble chamber typically change continuously and relatively slowly, it is hereby ensured that the base signal used for the detection of a needle disconnection properly reproduces the current status of the blood tubing kit.

Provision can furthermore be made that the base signal can be updated after a controlled change of the level in a bubble chamber of the extracorporeal blood circuit. The base signal can in this respect in particular be updatable after a venting of the bubble chamber. On the venting of a bubble chamber, the level within the bubble chamber increases relatively fast, which results in a correspondingly improved sound transfer via the bubble chamber and thus in an increase of the signal level. This is taken into account in accordance with the invention by an update carried out after such a change of the level.

The control and processing unit in this respect preferably carries out the updating automatically after the controlled level change was carried out. In this respect, the controlled level change and in particular the venting are also preferably carried out automatically by the control and processing unit.

The control and processing unit in this respect preferably generates the base signal on the basis of the signal generated by the structure-borne sound sensor, i.e. on the basis of the signal of the same sensor whose current signal is compared with the base signal.

Provision can in this respect be made in accordance with the invention that the control and processing unit forms an average time value of the measures signal for updating the base signal. Such an average time value provides that brief fluctuations of the signal remain out of consideration in the formation of the base signal. The reliability of a detection is hereby in turn improved.

This average time value of the measured signal is then updated in accordance with the present invention during the course of the treatment, for example at regular intervals or continuously. For this purpose, the respective signal development in a specific length of time preceding the updating can flow into the formation of the average time value.

The comparison of the currently measured signal with a base signal which is used for detecting a needle disconnection can then in this respect in accordance with the invention comprise an amplitude comparison. In this respect, the amplitude of the currently measured signal can in particular be compared with a base amplitude value. The control and processing unit can in this respect in particular form and store a base amplitude value before the start of the treatment and/or during the course of the treatment, with the currently measured amplitude being compared with said base amplitude value. Alternatively, the base signal can also be stored and a respective base amplitude value can be generated from the base signal to be compared with the current amplitude value.

In accordance with an aspect of the present invention, a signal portion of the measured signal can be extracted for the comparison of the currently measured signal with a base signal. This extracted signal portion is then preferably compared with the base signal or with a signal extracted from the base signal. In particular when a plurality of sound emitters are used, the signal originated from one of these emitters can in this respect be extracted to detect a needle disconnection with respect to this signal portion.

In accordance with the invention, the control and processing unit can in this respect in particular detect a needle disconnection when the sound propagation in the extracorporeal blood circuit changes due to the defective patient port and/or when the measured amplitude of the structure-borne sound reduces or is missing.

The control and processing unit in this respect preferably stops the blood pump and/or triggers an alarm on detection of a needle disconnection.

In accordance with a first possible embodiment of the present invention, the structure-borne sound emitter can be an occluding pump which can be coupled to a pump section of the tubing kit. Such occluding pumps generate strong pressure signals during their operation which propagate as sound-borne sound through the extracorporeal blood circuit. The occluding pump can in this respect in particular be a roller pump.

In a further possible embodiment, the structure-borne sound emitter can also be an electronically controlled sound generator. It can, for example, be coupled to the tubing kit upstream or downstream of a pump. The electronically controlled sound generator in this respect converts an electronic signal into a sound signal. The sound generator can in this respect in particular comprise a piezo-element. The pump can in this case also be a non-occluding pump, in particular an impeller pump. In this case, the sound waves generated by the electronically controlled sound generator also propagate over two propagation paths.

In accordance with a possible embodiment of the present invention, a single structure-borne sound emitter can be used in this respect whose signal propagates over the extracorporeal blood tubing kit and the patient port up to the structure-borne sound sensor. The signal can propagate in two paths in this respect; on the one hand, via the extracorporeal blood tubing kit and, on the other hand, via the patient port to the structure-borne sound sensor. In this respect, the structure-borne sound can in particular propagate on a first path via the extracorporeal blood tubing kit through a bubble chamber to the structure-borne sound sensor and, on the other hand, via a second path via the patient port to the structure-borne sound sensor, without passing through the bubble chamber.

The updating of the base signal in accordance with the invention in this embodiment takes account of the influence of the filling level of the bubble chamber on the signal portion which arrives at the structure-borne sound sensor over the first path.

The signal can, however, also propagate in only one path via the patient port to the structure-borne sound sensor. In this respect, the structure-borne sound can in particular pass through the bubble chamber before or after it has passed through the patient port so that the filling level of the bubble chamber influences the complete signal propagating through the patient port.

In accordance with the invention, however, two structure-borne sound emitters having different signal developments can also be used, in particular an occluding blood pump and a further structure-borne sound emitter arranged upstream or downstream of the blood pump.

In this respect, the signal portions attributable to the two structure-borne sound emitters are preferably separated and at least the signal portion based on the structure-borne sound emitter arranged closer to the patient port is used for monitoring the patient port. The signal of the structure-borne sound emitter which is arranged closer to the patient in the arterial line and thus conducts its signal directly via the patient port to the venous line can in particular be used in this respect.

In principle, an occluding blood pump can be used as a sound generator which generates strong pressure pulses upstream and downstream as is proposed in WO 97/10013 A1.

It has proved more reliable, however, to feed in a separate structure-borne sound signal having a defined frequency. A sinusoidal frequency in the frequency range of at least 80 Hz, in particular 160 Hz, has proved particularly suitable for the feed into the extracorporeal blood tubing kit. A rectangular pulse signal is also suitable.

In the case of a venous needle disconnection, a reduction in the measured amplitude of the structure-borne sound by around 30% can be expected at an extracorporeal blood circuit so that in this error case a significant indication of a venous needle disconnection is present. The control and processing unit in particular therefore concludes a needle disconnection when a reduction is recognized in the measured amplitude of the structural-borne sound by a threshold which lies between 20% and 60% of the base signal.

A piezo film sensor is, for example, suitable as a structure-borne sound sensor which can be coupled to the extracorporeal blood tubing kit.

The present invention in this respect furthermore comprises a blood treatment machine having a blood tubing kit such as was described above, wherein the blood tubing kit has at least one coupling point for a structure-borne sound emitter and at least one coupling point for a structure-borne sound sensor. The coupling point for the structure-borne sound emitter is in this respect advantageously arranged upstream of the blood pump at the arterial branch of the blood tubing kit or the blood pump itself serves as the structure-borne sound emitter.

In this respect, the coupling point for the structure-borne sound sensor can be arranged downstream of the venous bubble chamber. If the structure-born sound now propagates, starting from the structure-borne sound emitter, both in the arterial branch and in the venous branch of the extracorporeal blood tubing kit simultaneously, sound waves are thus incident onto the structure-borne sound sensor which have passed through the bubble chamber and other ones which have only passed through the patient port.

In an alternative embodiment, the coupling point for the structure-borne sound sensor is arranged upstream of the venous bubble chamber. In this case, the sound waves which propagate from the structure-borne sound emitter via the patient port into the venous line pass through the bubble chamber before arriving at the structure-borne sound emitter. The measured signal thus comprises signal portions which are based on passing through the bubble chamber and signal portions which are based on passing through the patient port. However, due to the updating of the base signal, the changes in the signal caused due to the level change in the bubble chamber can be taken into account on the detection of a needle disconnection.

The present invention furthermore comprises a method of monitoring the status of a patient port of an extracorporeal blood circuit of a blood treatment apparatus for the extracorporeal blood treatment, wherein the status of the patient port is monitored on the basis of the measurement of structure-borne sound at the extracorporeal blood circuit. In accordance with the invention, the currently measured signal is in this respect compared with a base signal, which is updated during the course of the treatment, for detecting a needle disconnection. The influence of the transfer behavior of the blood tubing kit and in particular the influence of the filling level of a bubble chamber on the sound propagation in the blood tubing kit can hereby also be taken into account in the detection of a needle disconnection.

The base signal is in this respect preferably updated at regular intervals and/or continuously. Provision can furthermore be made that the base signal is updated after a controlled change of the level in a bubble chamber of the extracorporeal blood circuit. This can in particular take place after a venting of the bubble chamber.

In accordance with the method of the invention, an average time value can furthermore be used for updating the base signal.

The comparison in accordance with the invention of the currently measured signal with a base signal can comprise an amplitude comparison. In this respect, the amplitude of the currently measured signal is preferably compared with a base amplitude value.

Furthermore, a signal portion of the measured signal can be extracted and compared with a base signal for the comparison of the currently measured signal with a base signal. In this respect, a signal portion which is based on one of a plurality of structure-borne sound emitters can in particular be extracted.

In accordance with the invention, in this respect a needle disconnection can particular be detected when the sound propagation in the extracorporeal blood circuit changes due to the defective patient port and/or when the measured amplitude of the structure-borne sound reduces or is missing. In this respect, the blood pump is preferably stopped and/or an alarm is triggered on detection of a needle disconnection. A venous needle disconnection can in particular be detected in accordance with the invention.

In accordance with the present invention, in a first possible variant, the signal of an occluding pump propagating through the extracorporeal blood circuit and the patient port can be measured. It can in this respect in particular be the signal of a roller pump. The occluding pump is in this respect coupled to a pump section of the tubing kit and generates pressure pulses which propagate as a structure-borne sound signal.

Alternatively or additionally, the signal of an electronically controlled sound generator can be measured. The sound generator can in this respect in particular comprise a piezo-element. The sound generator is preferably coupled to the tubing kit upstream or downstream of a pump. In this respect, the electronically controlled sound generator can in particular be controlled by a control signal and can convert it into a sound signal. The sound signal generated by the electronically controlled sound generator preferably differs from the signal generated by the pump.

In accordance with the invention, in this respect, both an occluding pump and an electronically controlled sound generator can be used as the structure-borne sound emitter. Alternatively, an electronically controlled sound generator can, however, also be used together with a non-occluding pump, in particular with an impeller pump.

In accordance with the present invention, the structure-borne sound emitter can be coupled to the arterial branch of the blood tubing kit and in particular upstream of the blood pump, and/or the blood pump can serve as the structure-borne sound emitter. The structure-borne sound sensor can be coupled downstream or upstream of the venous bubble chamber.

The method in accordance with the invention in this respect is preferably carried out as has already been shown in more detail with respect to the operation of the blood treatment apparatus in accordance with the invention. The method in accordance with the invention can in particular be used in this respect to monitor the status of a patient port of an extracorporeal blood circuit of a blood treatment apparatus such as has been shown above.

Figure 2:
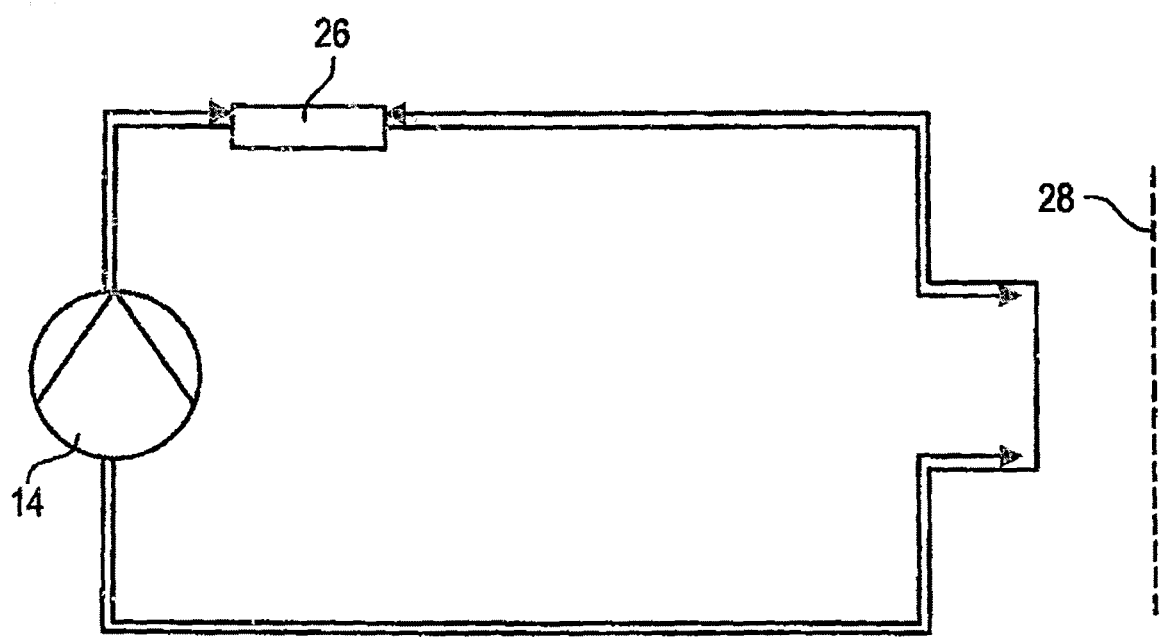
Figure 3:
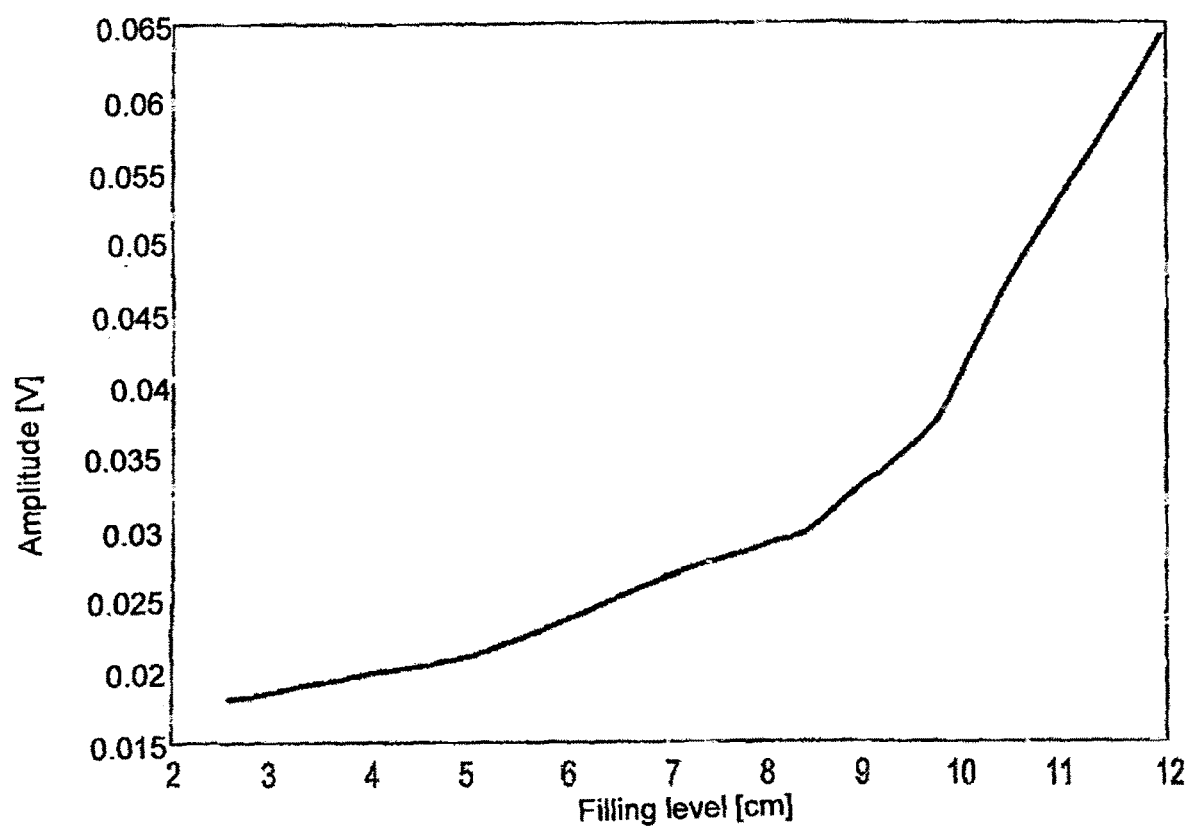
Figure 4:
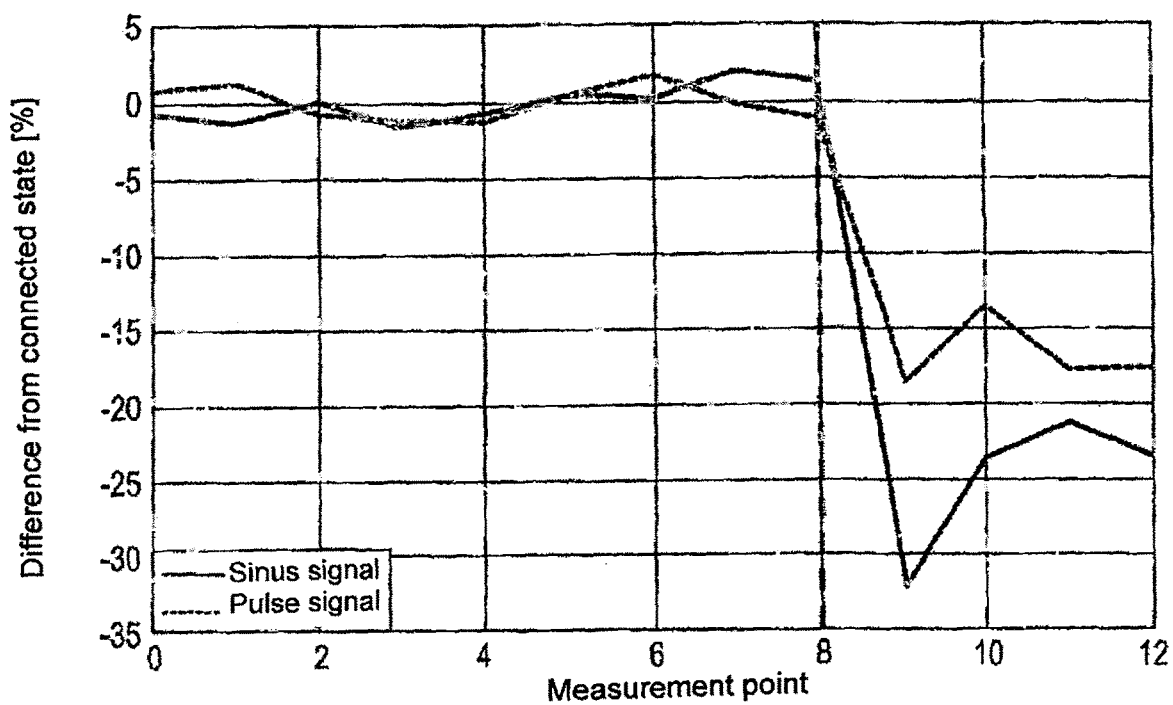
Figure 5:
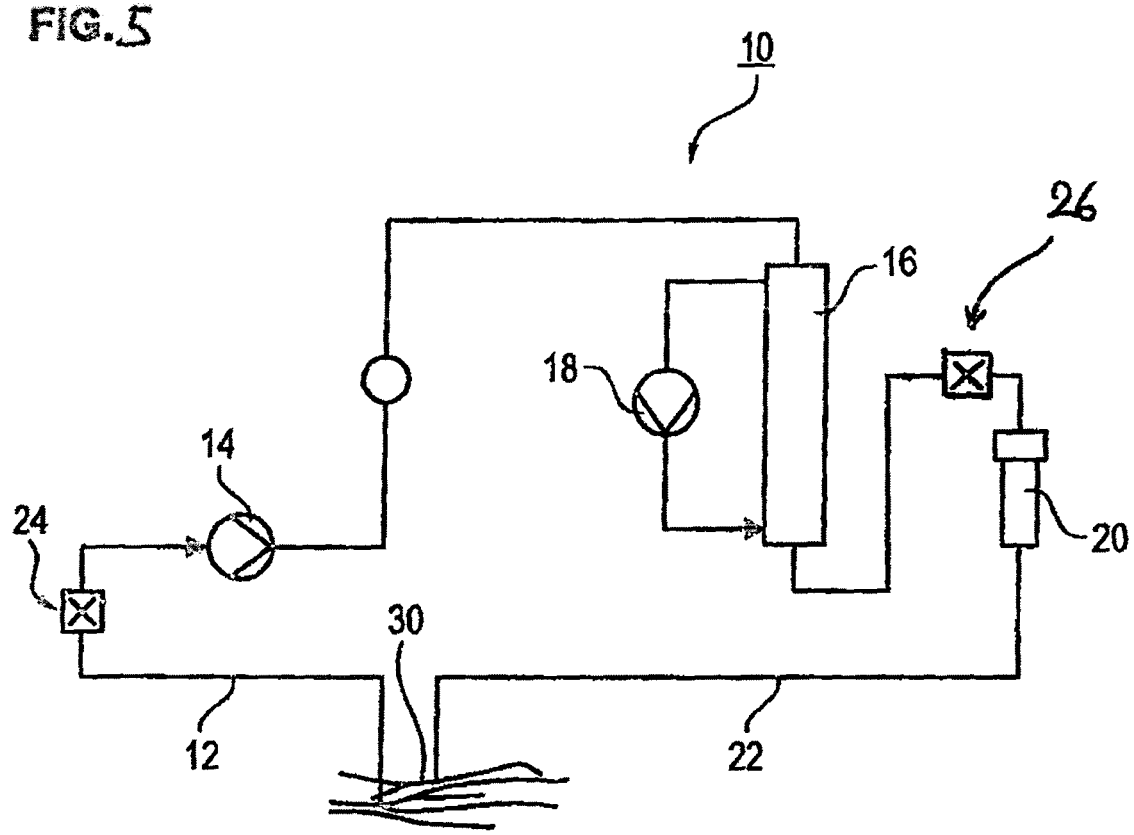

Further features, details and advantages of the invention result from the following description of the embodiments shown by the drawing. There are shown:

FIG. 1: the schematic representation of an extracorporeal blood circuit with exemplary positions of a structure-borne sound emitter and of a structure-borne sound sensor;

FIG. 2: a schematic representation of the propagation along the arterial branch and along the venous branch of the extracorporeal blood circuit of the structure-borne sound generated by the blood pump in an extracorporeal blood circuit up to the incidence on a structure-borne sound sensor downstream of the blood pump;

FIG. 3: the amplitude of the measured structure-borne sound after passing through a venous bubble chamber of an extracorporeal blood circuit in accordance with FIG. 1 in dependence on the filling level of the blood in the bubble chamber;

FIG. 4: measured values of the relative reduction of the measured structure-borne sound after passing through an extracorporeal blood circuit and through the patient port in accordance with FIG. 1 in dependence on the time on an occurrence of a needle disconnection after a time of t=8 sec.; and FIG. 5: the schematic representation of an extracorporeal blood circuit with alternative exemplary positions of a structure-borne sound emitter and of a structure-borne sound sensor.

FIG. 1 very generally shows in a schematic representation an extracorporeal blood circuit 10 in which an arterial tube 12 is in communication with an artery of a patient. A blood pump 14 and a dialyzer 16 are shown in a typical manner here. A dialyzate pump 18 is shown parallel to the dialyzer. A bubble chamber 20 is connected downstream of the dialyzer. Said bubble chamber is adjoined by a venous tube 22 which is in turn connected to a corresponding vein of the patient.

A structure-borne sound emitter 24 and a structure-borne sound sensor 26 are now arranged in the extracorporeal blood circuit 10. They serve to determine the propagation of the structure-borne sound in the extracorporeal blood tubing kit using a control and processing unit not shown in any more detail here. The structure-borne sound can be coupled into the blood tubing kit, for example, by means of a sound source at the blood treatment apparatus. A suitable coupling point for the structure-borne sound can take place in the arterial branch of the blood tubing kit upstream of the blood pump, i.e. approximately 30 cm upstream of the blood pump in accordance with the embodiment shown here. The structure-borne sound emitter 24 is therefore arranged approximately 30 cm upstream of the blood pump 14 (cf. FIG. 1).

A possible position of a structure-borne sound sensor 26 can be provided downstream of the venous bubble chamber 20 as likewise shown in FIG. 1. The length of the venous tube 22 still has a length of approximately 1.6 m from the desired sensor position onward. The structure-borne sound emitter and the structure-borne sound sensor can in particular be integrated in the blood treatment apparatus so that they can each be coupled to the provided coupling points at the extracorporeal blood tubing kit on the insertion of an extracorporeal blood tubing kit. This is not shown in detail in the schematic representation in accordance with FIG. 1.

The walls of the components of the extracorporeal blood circuit 10 have a more damping effect on the sound propagation in comparison with the sound conduction of the fluid in the blood tubing kit. It has been shown that the damping behavior of the venous blood chamber 20 is significantly and reproducibly amplified as the filling level falls. The higher the filling level is, the lower the damping. The present invention is therefore based on the fact that a conclusion is drawn from the measured damping behavior of the bubble chamber 20 on its filling level. The damping behavior is determined in that the amplitude of the structure-borne sound is measured downstream of the bubble chamber to be measured in a sound propagation direction, with the measured structure-borne sound being damped at different levels in dependence on the filling level on passing through the bubble chamber 20. The measured amplitude of the structure-borne sound is shown in dependence on the filling level of an exemplary bubble chamber 20 in FIG. 3, with the amplitude of the structure-borne sound being measured downstream of the bubble chamber in the direction of the blood flow. The measured amplitude of the structure-borne sound progressively increases in the exemplary bubble chamber as the filling level of the bubble chamber increases because the damping of the sound waves reduces accordingly. A corresponding characteristic can be stored in the control and processing unit, not shown here in any more detail, of the blood treatment machine so that the filling level in the bubble chamber can be calculated from current measured values of the amplitude of the structure-borne sound.

The propagation of the structure-borne sound generated by the blood pump in an extracorporeal blood circuit is shown very schematically here in FIG. 2 along the arterial branch and along the venous branch of the extracorporeal blood circuit up to the incidence on a structure-borne sound sensor downstream of the blood pump. A piezo film sensor can be used as the sensor 26 here. A shunt 28, not shown in any more detail, is shown very generally by the dashed line.

In accordance with a further aspect of the invention a needle disconnection, in particular an arterial and/or venous needle disconnection can also be detected, when the sound transmission in the extracorporeal blood circuit varies due to the defective patient port and when the measured amplitude of the structure-borne sound reduces or is even lost. In the case of a venous needle disconnection (cf. FIG. 1 and here in particular the reference numeral 30), a reduction in the measured amplitude of the structure-borne body sound by around 30% can be expected at an extracorporeal blood circuit so that in this error case a significant indication of a venous needle disconnection is present as becomes clear with reference to the representation of FIG. 4. The needle disconnection is shown here by a dashed line after a time of t=8 sec.

In accordance with the present invention, the detection of a needle disconnection and the filling level measurement in the bubble chamber can in this respect be combined with one another or the influence of the sound conductivity of the blood tubing kit in the detection of a needle disconnection can be taken into account.

In accordance with the invention, it was recognized in this respect that the signal of the structure-borne sound emitter is also transferred via the tube line or wall of the bubble chamber and thus not only influences the measured signal at the other side of the blood pump, dialyzer and bubble chamber, but even additionally allows a determination of the level status in the bubble chamber.

In accordance with the invention, in addition to the level determination in the bubble chamber, the status of the patient port and in particular the arterial and/or venous connection of the blood tubing kit to the patient can therefore simultaneously be monitored.

In the embodiment shown in FIGS. 1 to 2, the signal path over the patient port 30 does not run through the bubble chamber 20 since the latter lies in the venous line behind the structure-borne sound sensor 26 starting from the patient port. The strength of the signal from the structure-borne sound emitter 24 arriving at the structure-borne sound sensor 26 via the patient port 30 therefore does not depend on the level status in the bubble chamber 20.

However, the pump 14 can in a first embodiment be a non-occluding pump so that the signal of the structure-borne sound emitter 24 also arrives at the structure-borne sound sensor 26 via the extracorporeal blood circuit and in particular the dialyzer 16 and the bubble chamber 20. The signal present at the structure-borne sound sensor 26 is thus a superimposition of the signal portion running through the patient port 30 and of the signal portion running through the bubble chamber 20. Since the signal portion running through the bubble chamber depends on the level status of the bubble chamber, the total signal which is measured by the structure-borne sound sensor 26 also depends on the level status.

The same applies to the embodiment shown in FIG. 5 in which the structure-borne sound sensor 26 is arranged between the dialyzer 16 and the venous bubble chamber 20 and thus, viewed from the patient port, behind the venous bubble chamber 20. In this embodiment, the total signal which runs from the structure-borne sound emitter 24 over the patient port 30 to the structure-borne sound sensor 26 thus runs through the bubble chamber so that its strength depends on the filling level of the bubble chamber.

Depending on whether the pump 14 is an occluding pump or a non-occluding pump, a signal portion of the signal transmitted by the structure-borne sound emitter 24 in this respect arrives at the structure-borne sound sensor 26 over the dialyzer 16 in the embodiment shown in FIG. 5. This signal portion is, however, at least not influenced by the level status in the venous bubble chamber 20. An arterial bubble chamber is, however, optionally provided here whose level status would then influence this signal portion.

If, in contrast, an occluding pump 14 is used in FIG. 5, the structure-borne sound generated by the structure-borne sound emitter 24 then arrives at the structure-borne sound sensor 26 almost exclusively via the patient port 30 since the occluding pump 14 blocks the transfer of the structure-borne sound from the structure-borne sound emitter 24.

In any case, however, in the above-shown embodiments, the filling level in the bubble chamber has an influence on the signal of the structure-borne sound emitter 24 arriving at the structure-borne sound sensor 26. The same situation also results when in further alternative embodiments an occluding blood pump 14 is used as the structure-borne sound emitter instead of a separate structure-borne sound emitter 24. Independently of whether the structure-borne sound sensor 26 is then arranged upstream or downstream of the venous bubble chamber 20, one of the two signal portions which is emitted by the occluding pump namely always arrives at the structure-borne sound sensor 26 via the bubble chamber 20.

It is, however, possible in accordance with the present invention both to determine the level status in the bubble chamber 20 and to monitor the patient port 30 using the signal of the structure-borne sound sensor 26. In this respect, the measurement is substantially based on the recognition that the measured amplitude admittedly falls or rises in dependence on the level statuses in the bubble chamber, which takes place, however, continuously and at a much lower frequency and strength than the amplitude leap which takes place on a needle disconnection, in particular on a venous needle disconnection. The two processes can hereby be easily distinguished from one another by a corresponding evaluation of the signal.

To detect the strong amplitude change of a needle disconnection, a baseline or a base signal is determined and tracked during the operation of the blood treatment apparatus. In accordance with the invention, the baseline is in this respect determined from the signal generated by the structure-borne sound sensor 26. The baseline preferably reflects the long-term change of the signal by the updating and thus in particular represents an average time value.

This baseline is in this respect updated at regular intervals and on controlled level changes in the drip chamber. The baseline can in this respect also be updated continuously or in that it is determined as an average time value over a respective preceding time period of predefined duration, for example over the last 10 to 20 sec.

The connection of the patient is monitored in that the signal currently measured by the structure-borne sound sensor 26 is compared with the baseline. If a substantial drop of the currently measured signal beneath the baseline takes place here, for example a drop of more than 30%, a conclusion on a needle disconnection is drawn herefrom. The blood treatment apparatus thereupon stops the blood pump and optionally triggers an alarm.

The level status in the drip chamber can furthermore be determined from the baseline. The level status can in this respect in particular be determined with reference to the current value of the baseline via a characteristic stored in the control.

The recognition underlying the present invention that the filling level in the bubble chamber and overall the status of the extracorporeal blood tubing kit has an effect on the signal measured by the structure-borne sound sensor 26 so that the measured signal can also change during the treatment with a correct connection of the patient, can, however, also be used in accordance with the invention without a determination of the filling level in the bubble chamber to improve the detection of a needle disconnection.

A baseline can in particular also be determined here as described above and the currently measured signal can be compared with this baseline for monitoring the connection. In accordance with the invention, the baseline is in this respect updated during the operation of the blood treatment device in order thus to make the detection of a needle disconnection robust toward changes at the blood tubing kit such as a change of the level status of the bubble chamber.

The baseline can in this respect in particular be determined as was described above. The baseline is in this respect in particular formed from the signal of the structure-borne sound sensor 26 whose signal is also used for detecting the disconnection by comparison with the baseline. The signal can in this respect be updated at regular intervals and/or after a controlled level change in the bubble chamber, i.e. in particular when the level increases by venting the bubble chamber. In this respect, a signal averaged over time can be used as the baseline. The baseline can in this respect also optionally be measured continuously in that a respective signal averaged over a certain preceding time period is used as the baseline. Accordingly, for detecting a needle disconnection in this embodiment, the current signal value is compared with an average value of the signal over a respective preceding time period of predefined duration.

The evaluation can in this respect take place with reference to the amplitude of the signal. Optionally, however, a signal preparation can also precede the evaluation, for example the extraction of a specific frequency range in order thus to be able to distinguish the signal transmitted by the structure-borne sound emitter from other signals.

In the above-shown embodiments, the level status of the bubble chamber in this respect had a respective effect at least on a portion of the signal transmitted by the structure-borne sound emitter 24 and arriving at the structure-borne sound sensor 26.

If, however, in the embodiment shown in FIG. 1, an occluding pump is used as the blood pump 14, it largely bocks the signal of the structure-borne sound emitter 24 propagating in the direction of flow through the extracorporeal blood tubing kit so that it arrives at the structure-borne sound sensor 26 almost exclusively over the patient port 30. The blood pump 14, however likewise generates pressure pulses which propagate in both directions through the circuit. On a first signal path, the pressure pulses which likewise represent structure-borne sound in the sense of the present invention run through the dialyzer 16 and arrive at the structure-borne sound sensor 26 via the bubble chamber 20. On the second signal path, the pressure pulses of the pump propagate via the patient port 30 and the venous line 22 to the structure-borne sound sensor 26.

The structure-borne sound emitter 24 is therefore preferably operated such that its signal can be clearly distinguished from the signal of the blood pump. Another frequency can in particular be used here than that which generates the blood pump. The two signal portions based on the structure-borne sound emitter 24 and on the blood pump can therefore be separated from the signal measured by the structure-borne sound sensor 26 and can be evaluated separately, for example by a corresponding frequency separation. The signal generated by the structure-borne sound emitter 24 can then be used exclusively for detecting a needle disconnection. The signal of the blood pump 14 serving as the second structure-borne sound emitter can then be used for determining the level status, and optionally for the disconnection of the patient in addition to a second detection stage.

Independently of the specific design, the processes which vary the signal at the structure-borne sound sensor 26 can therefore be associated either with a level status change in the drip chamber or with a needle disconnection. The respective other signal can in this respect also serve as a reference for a side, e.g. for determining a baseline. A common evaluation of a function which depends on both signals, e.g. as a quotient, can also take place.

The invention claimed is:

1. A medical device, having (a) a control and processing unit, (b) at least one structure-borne sound emitter, (c) at least one structure-borne sound sensor, and (d) a tubing kit wherein the at least one structure-borne sound emitter and at least one structure-borne sound sensor are configured for coupling to coupling points of the tubing kit, the tubing kit comprising at least one bubble chamber, at least a first coupling point for the structure-borne sound emitter arranged before the bubble chamber, and at least a second coupling point for the structure-borne sound sensor arranged in a structure-borne sound propagation direction after the bubble chamber, characterized in that the control and processing unit is configured such that a filling level of the bubble chamber arranged in the tubing kit can be determined via the control and processing unit based on a measurement of the structure-borne sound at the tubing kit by coupling a structure-borne sound by the structure-borne sound emitter via the first coupling point into the tubing kit before the bubble chamber; and the structure-borne sound propagating in the fluid circuit is taken up by the structure-borne sound sensor coupled to the second coupling point arranged in the structure-borne sound propagation direction after the bubble chamber and is supplied to the control and processing unit for determining the filling level.

2. A medical device in accordance with claim 1, wherein the control and processing unit is configured to determine the filling level of the bubble chamber by comparison with at least one stored characteristic, the stored characteristic associating different fluid levels with different amplitudes of a signal of the structure-borne sound sensor.

3. A medical device in accordance with claim 1, wherein the structure-borne sound emitter is an occluding pump, which can be coupled to a pump section of the tubing kit.

4. A medical device in accordance with claim 1, wherein the medical device is a dialysis apparatus for dialysis blood treatment and the tubing kit further comprises a dialyser.

5. A medical device in accordance with claim 4, wherein the tubing kit comprises a patient port, and wherein the control and processing unit is furthermore configured to monitor the status of the patient port.

6. A medical device in accordance with claim 5, wherein the control and processing unit is further configured to evaluate a signal of the structure-borne sound sensor in different manners for monitoring the patient port in order to detect a needle disconnection and for the simultaneous determination of the filling level of the bubble chamber.

7. A medical device in accordance with claim 6, wherein the control and processing unit is configured to monitor the signal of the structure-borne sound sensor for faster amplitude changes for detection of the needle disconnection, whereas and wherein the control and processing unit is further configured to detect changes in the filling level of the bubble chamber with reference to slower amplitude changes.

8. A medical device in accordance with claim 6, wherein two structure-borne sound emitters having different signal developments are used, wherein the control and processing unit is further configured to separate respective signal portions attributable to the two structure-borne sound emitters and to evaluate the signal portions separately for monitoring the patient port and for the simultaneous determination of the filling level of the bubble chamber.

9. A medical device in accordance with claim 1, characterized in that the at least one emitter and the at least one sensor are integrated into coupling points of the medical device such that they are coupled to the tubing kit on insertion of fluid lines of the tubing kit to the coupling points of the medical device.

10. A medical device in accordance with claim 1 having a tubing kit, characterized in that the tubing kit has the at least one coupling point for a structure-borne sound emitter arranged in a first fluid line, at the least one bubble chamber and at least one coupling point for a structure-borne sound sensor arranged in a second fluid line.

11. A medical device in accordance with claim 10, characterized in that the coupling point for the structure-borne sound emitter at an arterial branch of the tubing kit is arranged upstream of the blood pump and the bubble chamber is arranged downstream of the blood pump; or characterized in that a pump segment of the tubing kit is used as a coupling point for the blood pump serving as the structure-borne sound emitter.

12. A method for detecting the filling level of a bubble chamber in a fluid circuit of the medical device according to claim 1, characterized in that a structure-borne sound is coupled by a structure-borne sound emitter via a first coupling point into a tubing kit, before a bubble chamber; and in that the structure-borne sound propagating in the fluid circuit is taken up by a structure-borne sound sensor coupled to a second coupling point arranged in a structure-borne sound propagation direction after the bubble chamber and is conducted to a control and processing unit for determining the filling level.

13. A method in accordance with claim 12, characterized in that the filling level of the liquid in the bubble chamber is determined in a control and processing unit of the blood treatment apparatus by a comparison with stored characteristics.

14. A method in accordance with claim 12 for detecting the filling level of a bubble chamber in an extracorporeal blood circuit in a blood treatment having a control and processing unit, at least one structure-borne sound emitter and at least one structure-borne sound sensor, each configured for coupling to coupling points of a medical tubing kit which can be coupled to the medical device, the filling status of the bubble chamber arranged in the tubing kit determined via the control and processing unit on the basis of the measurement of the structure-borne sound at the tubing kit.

15. A computer program product comprising a source code for carrying out the method in accordance with claim 12 when the computer program runs in a control and processing unit of the medical device.

16. A medical device in accordance with claim 1, characterized in that the medical device is a blood treatment apparatus.

17. A medical device in accordance with claim 3, wherein the structure-borne sound emitter is an electronically controlled sound generator which comprises a piezo-element.

18. A medical device in accordance with claim 5, wherein the patient port comprises a needle connecting the tubing kit to patient, and wherein the control and processing unit is configured to detect a needle disconnection when an amplitude of the structure-borne sound measured by the structure-borne sound sensor reduces or is missing.

19. A medical device in accordance with claim 18, characterized in that the control and processing unit stops the blood pump and/or triggers an alarm on detection of a needle disconnection.

20. A medical device in accordance with claim 6, wherein the control and processing unit is configured to associate at least one out of different signal portions of the signal of the structure-borne sound sensor and changes in the signal of the structure-borne sound sensor differing in their time development with the monitoring of the patient port and the determination of the filling level of the bubble chamber.

21. A medical device in accordance with claim 7, wherein the control and processing unit is configured to compare, for detection of the needle disconnection, a currently measured signal with a base signal, and wherein the control and processing unit is configured to detect changes in the filling level of the bubble chamber by evaluating amplitude changes of the base signal.

22. A medical device in accordance with claim 8, wherein the two-structure-borne sound emitters are an occluding blood pump and a further structure-borne sound emitter arranged upstream of the blood pump.

23. A method in accordance with claim 12, wherein the fluid circuit of a medical device is an extracorporeal blood circuit in a blood treatment apparatus.

24. A medical device in accordance with claim 21, wherein the base signal is updated at least once during a course of a treatment and formed based on an average value over time.

25. A medical device in accordance with claim 1, wherein the tubing kit comprises a first fluid tubing line and a second fluid tubing line, the first fluid tubing line and the second fluid tubing line being in fluid connection with the bubble chamber, wherein the first coupling point for the structure-borne sound emitter is arranged in the first fluid tubing line before the bubble chamber and the second coupling point for the structure-borne sound sensor is arranged in the structure-borne sound propagation direction after the bubble chamber in the second fluid tubing line.

26. A medical device in accordance with claim 1, comprising a pump configured to pump fluid in at least one out of the flowing directions:
   a) from the first fluid tubing line via the bubble chamber to the second fluid tubing line, and
   b) from the second fluid tubing line via the bubble chamber to the first fluid tubing line.

27. A medical device in accordance with claim 1, wherein the control and processing unit is configured to determine a filling level value of the bubble chamber out of a plurality of different filling level values, wherein the control and processing unit is configured to associate the different filling level values with different levels of an amplitude of a signal measured by the structure-borne sound sensor.

28. A medical device in accordance with claim 27, wherein the control and processing unit is configured to associate progressively increasing filling level values with progressively increasing levels of the amplitude of the signal measured by the structure-borne sound sensor.

* * * * *